US010449305B2

(12) United States Patent
Aneas

(10) Patent No.: US 10,449,305 B2
(45) Date of Patent: Oct. 22, 2019

(54) DEVICE FOR PROTECTING A NEEDLE, SYRINGE PROVIDED WITH SUCH A DEVICE, AND METHOD FOR PRODUCING PRE-FILLED CEMENTED NEEDLE SYRINGES

(71) Applicant: BIOCORP PRODUCTION, Issoire (FR)

(72) Inventor: Antoine Aneas, Menetrol (FR)

(73) Assignee: BIOCORP PRODUCTION, Issoire (FR)

( * ) Notice: Subject to any disclaimer, the term of this patent is extended or adjusted under 35 U.S.C. 154(b) by 153 days.

(21) Appl. No.: 15/655,291

(22) PCT Filed: Jan. 25, 2016

(86) PCT No.: PCT/EP2016/051408
§ 371 (c)(1),
(2) Date: Jul. 20, 2017

(87) PCT Pub. No.: WO2016/120185
PCT Pub. Date: Aug. 4, 2016

(65) Prior Publication Data
US 2018/0147366 A1 May 31, 2018

(30) Foreign Application Priority Data

Jan. 26, 2015 (FR) ..................................... 15 50575
Jun. 2, 2015 (FR) ..................................... 15 54990

(51) Int. Cl.
*A61M 5/32* (2006.01)
*A61M 5/00* (2006.01)
*A61M 5/31* (2006.01)

(52) U.S. Cl.
CPC ............ *A61M 5/326* (2013.01); *A61M 5/002* (2013.01); *A61M 5/008* (2013.01);
(Continued)

(58) Field of Classification Search
CPC .... A61M 2005/312; A61M 2005/3267; A61M 2207/00; A61M 5/002; A61M 5/008;
(Continued)

(56) References Cited

U.S. PATENT DOCUMENTS 7,094,223 B2   8/2006   Brunel
8,118,788 B2   2/2012   Frezza
(Continued)

FOREIGN PATENT DOCUMENTS

CN   1446110 A     10/2003
CN   102464145 A    5/2012
(Continued)

OTHER PUBLICATIONS

English translation of International Preliminary Report on Patentability dated Feb. 9, 2017.
(Continued)

*Primary Examiner* — Brandy S Lee
(74) *Attorney, Agent, or Firm* — Pwarne & Gordon LLP

(57) ABSTRACT

The invention relates to a method for producing pre-filled cemented needle syringes, comprising the following steps: a device (D) for protecting the needle onto syringe bodies (2), the device comprising an external sleeve which can move along a longitudinal axis between a forward position in which it covers the needle, and a retracted position in which it does not cover the needle, means for returning the sleeve to the forward position, and a needle protector; arranging the syringe bodies (2), which are provided with the protective device, in recesses (O204) provided in a holder (200); placing the holder (200) in a container (100) for transport; removing the holder from the container; filling each syringe body with an active principle; inserting a plunger into each syringe; and removing the syringes (1) from their holder for the purpose of inspection and labelling.

15 Claims, 14 Drawing Sheets

Figure 1:
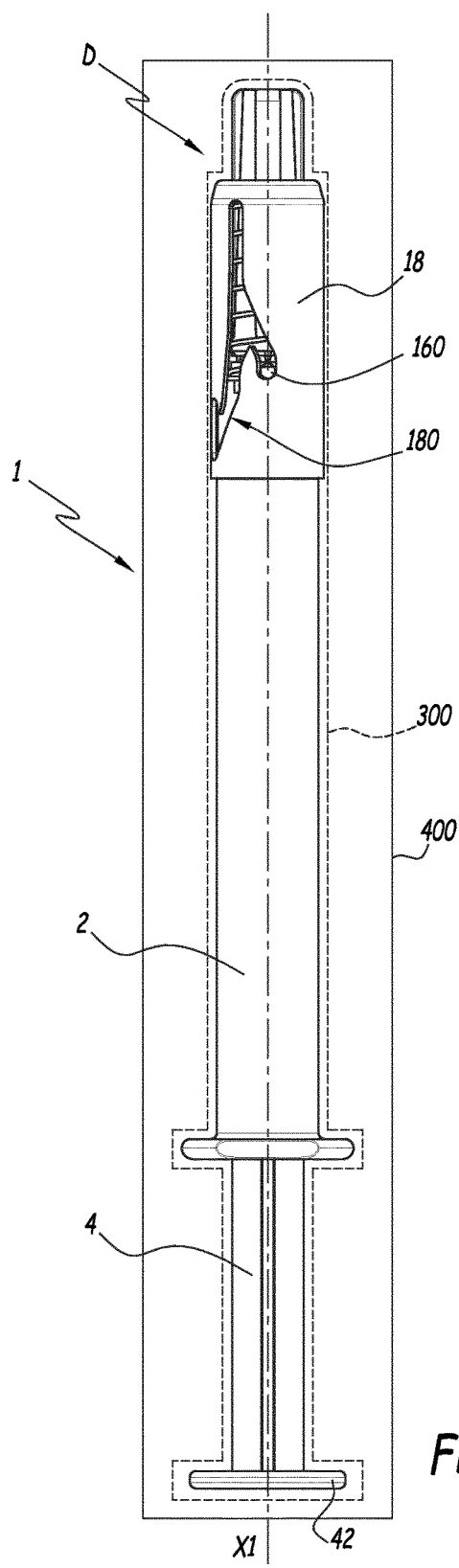

(52) U.S. Cl.
CPC ........ *A61M 5/3202* (2013.01); *A61M 5/3204* (2013.01); *A61M 5/3272* (2013.01); *A61M 2005/312* (2013.01); *A61M 2005/3267* (2013.01); *A61M 2207/00* (2013.01)

(58) Field of Classification Search
CPC .. A61M 5/3202; A61M 5/3204; A61M 5/326; A61M 5/3272
See application file for complete search history.

(56) References Cited

U.S. PATENT DOCUMENTS

| | | |
|---|---|---|
| 8,485,357 B2 | 7/2013 | Song et al. |
| 9,186,462 B2 | 11/2015 | Lanzi et al. |
| 2012/0118777 A1 | 5/2012 | Kakiuchi |

FOREIGN PATENT DOCUMENTS

| | | | |
|---|---|---|---|
| CN | 102470206 A | | 5/2012 |
| CN | 103002935 A | | 3/2013 |
| EP | 2452708 A1 | | 5/2012 |
| EP | 2974761 A1 | | 1/2016 |
| GB | 2114006 A | * | 8/1983 ............ A61M 5/326 |
| GB | 2114006 A | | 8/1983 |
| RU | 2008132971 A | | 2/2010 |
| WO | 03068298 A1 | | 8/2003 |
| WO | 2007077463 A1 | | 12/2007 |
| WO | 2008067467 A2 | | 6/2008 |
| WO | 2010019936 A1 | | 2/2010 |
| WO | 2011007194 A1 | | 1/2011 |
| WO | 2011110872 A1 | | 9/2011 |
| WO | 2011157930 A1 | | 12/2011 |
| WO | 2013084792 A1 | | 6/2013 |
| WO | 2013104736 A1 | | 7/2013 |
| WO | 2013134465 A1 | | 9/2013 |
| WO | 2014096825 A1 | | 6/2014 |
| WO | 2014131987 A1 | | 9/2014 |
| WO | 2014141470 A1 | | 9/2014 |
| WO | 2016115477 A2 | | 7/2016 |

OTHER PUBLICATIONS

International Search Report for PCT/EP2016/051408 dated Aug. 17, 2016.
International Written Opinion for PCT/EP2016/051408 dated Jan. 26, 2016.
Rapport Préliminaire International Sur La Brevetabilité for PCT/EP2016/051408 dated Jan. 26, 2015.

* cited by examiner

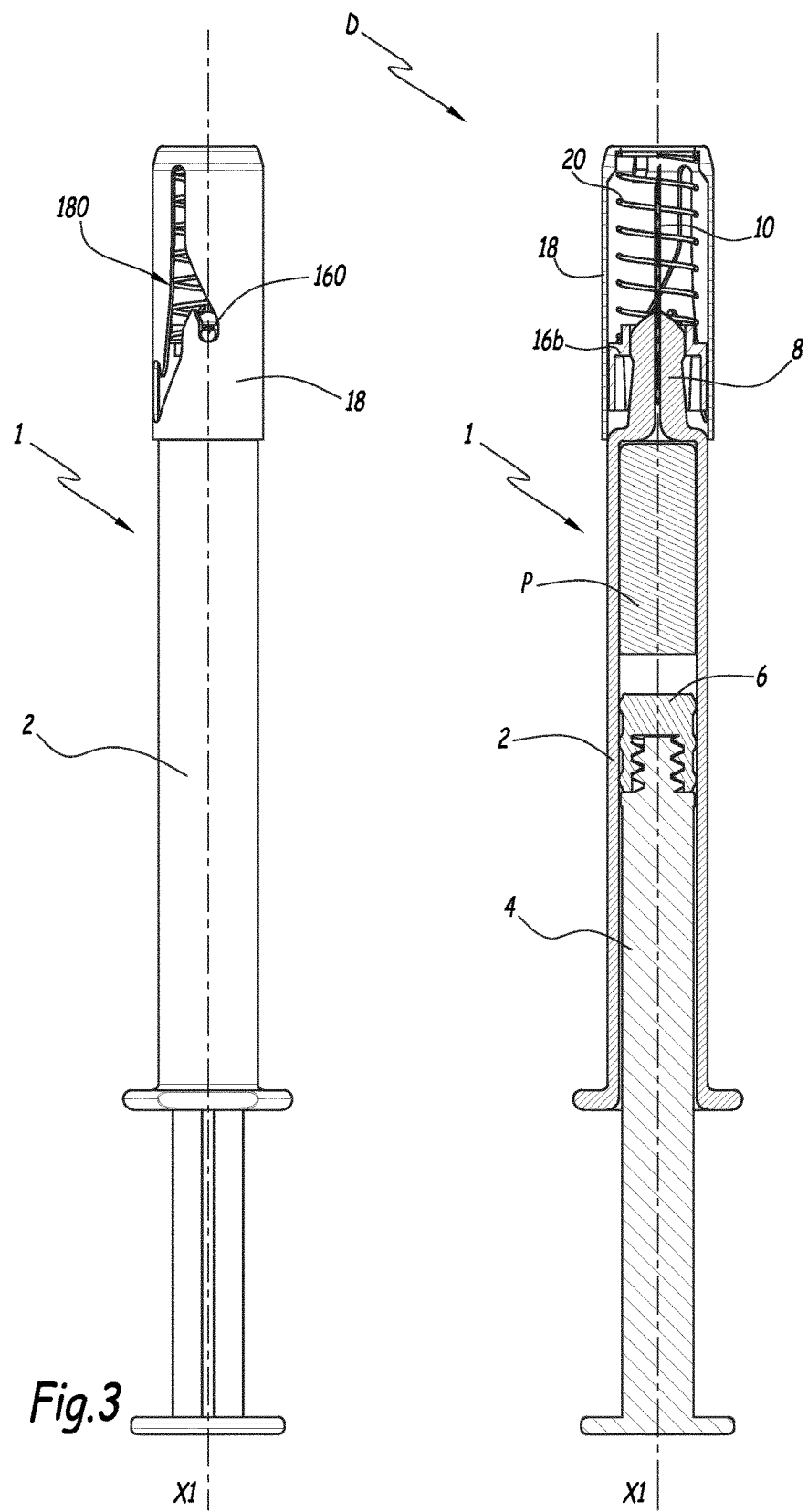

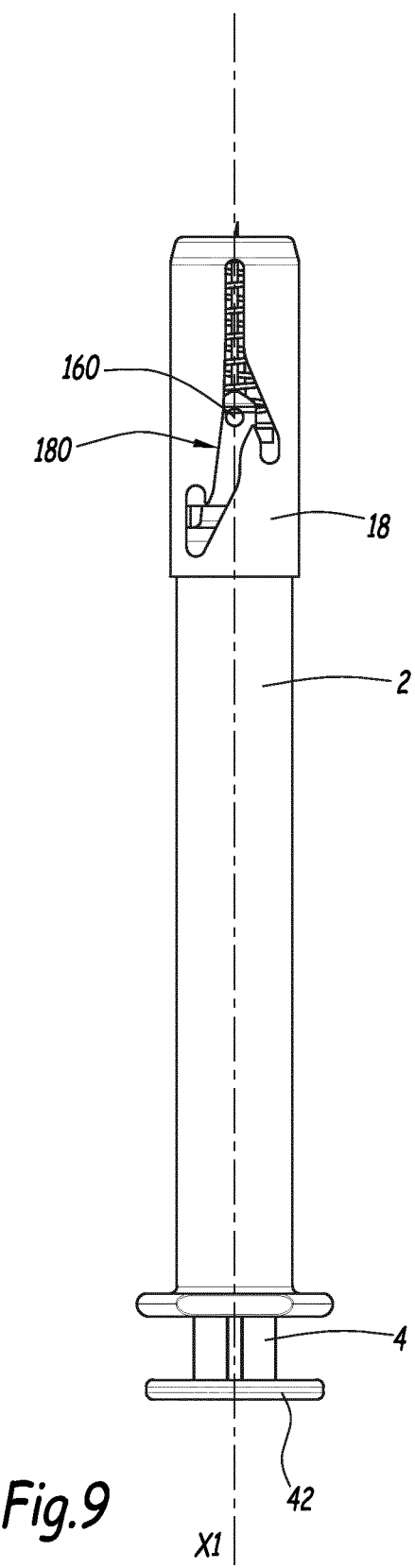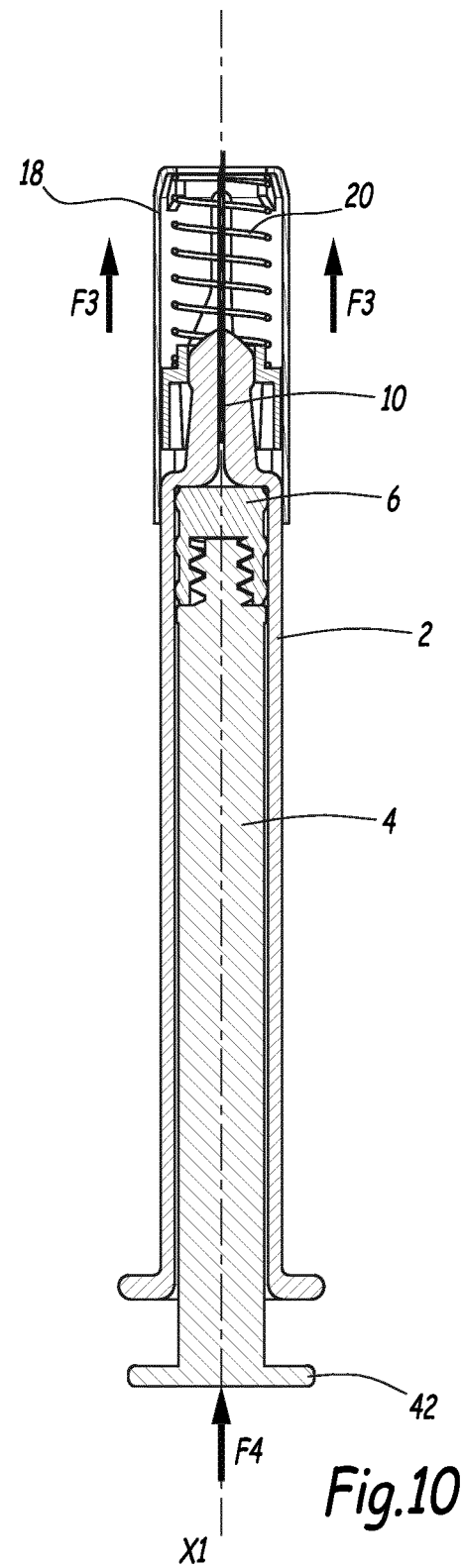
Fig.9
Fig.10

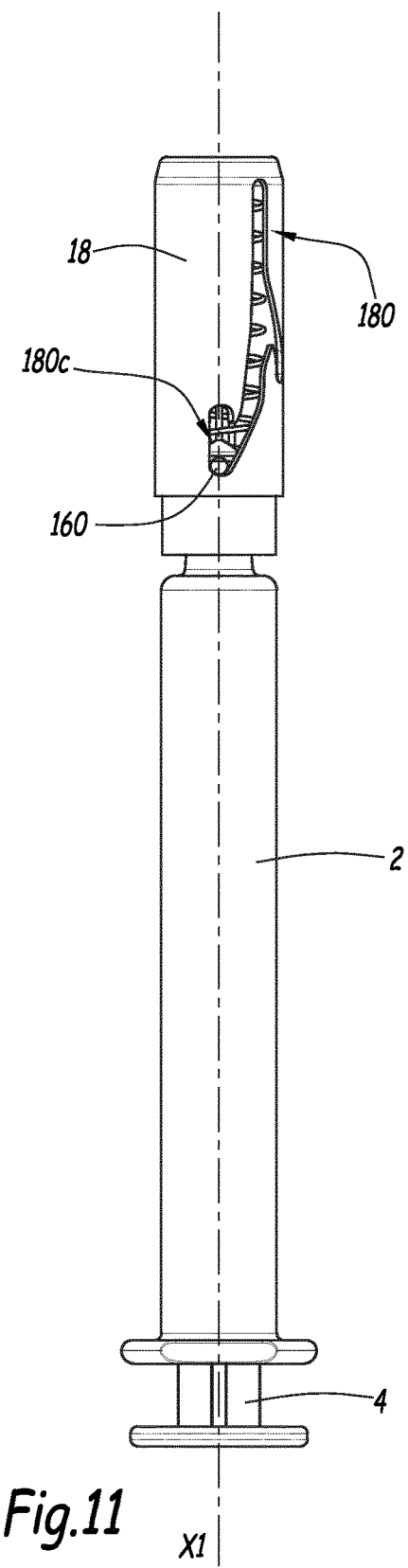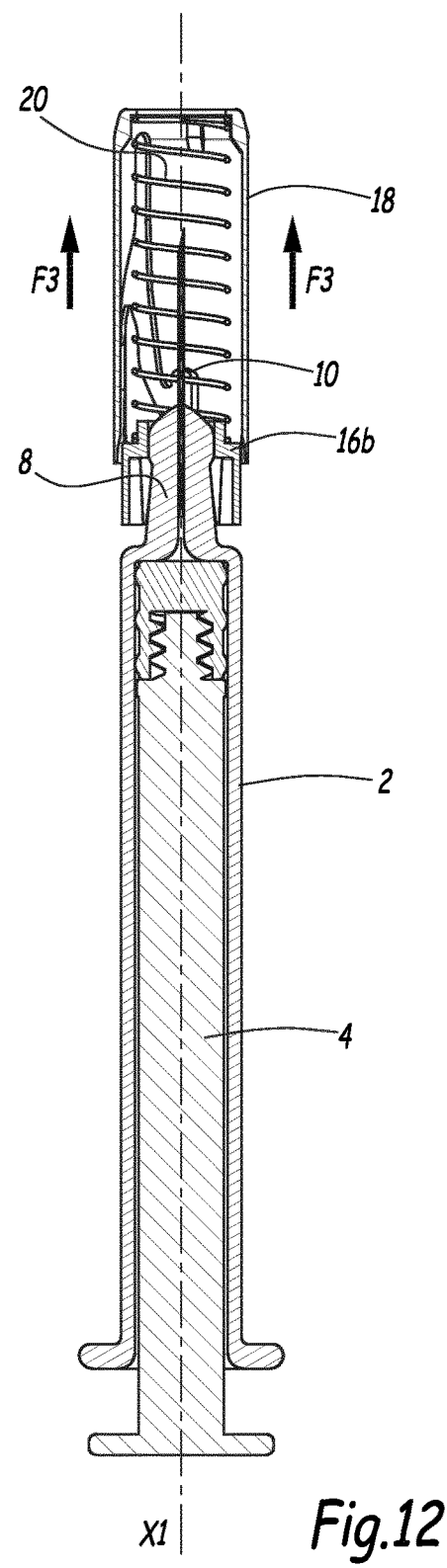
Fig.11
Fig.12

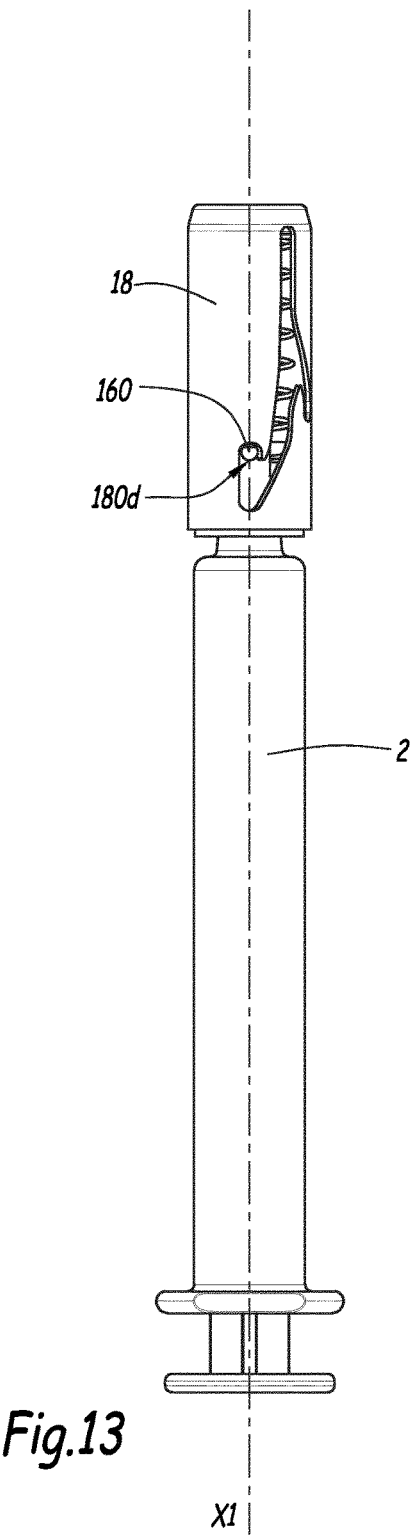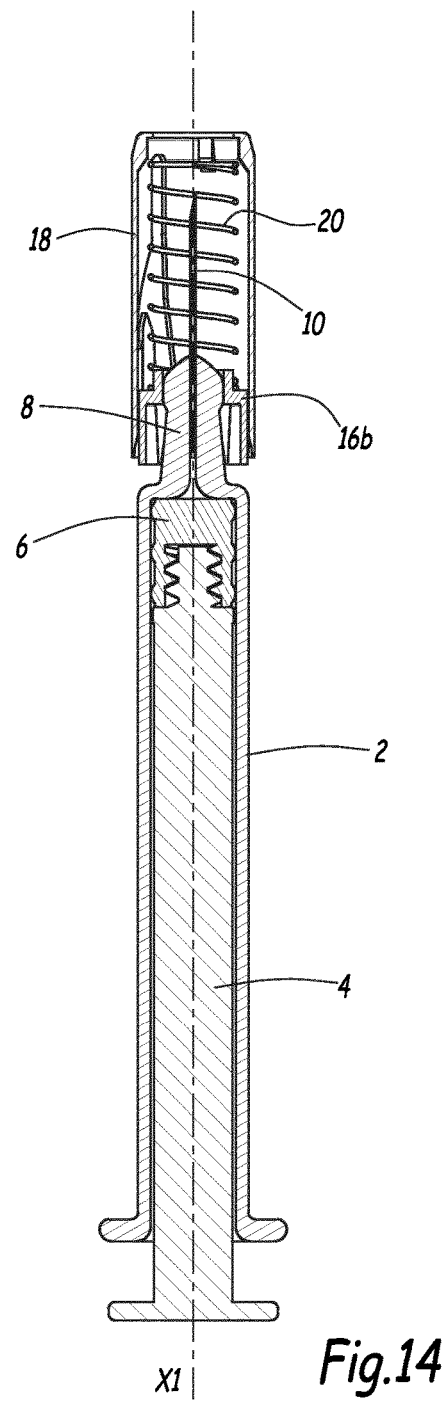
Fig.13
Fig.14

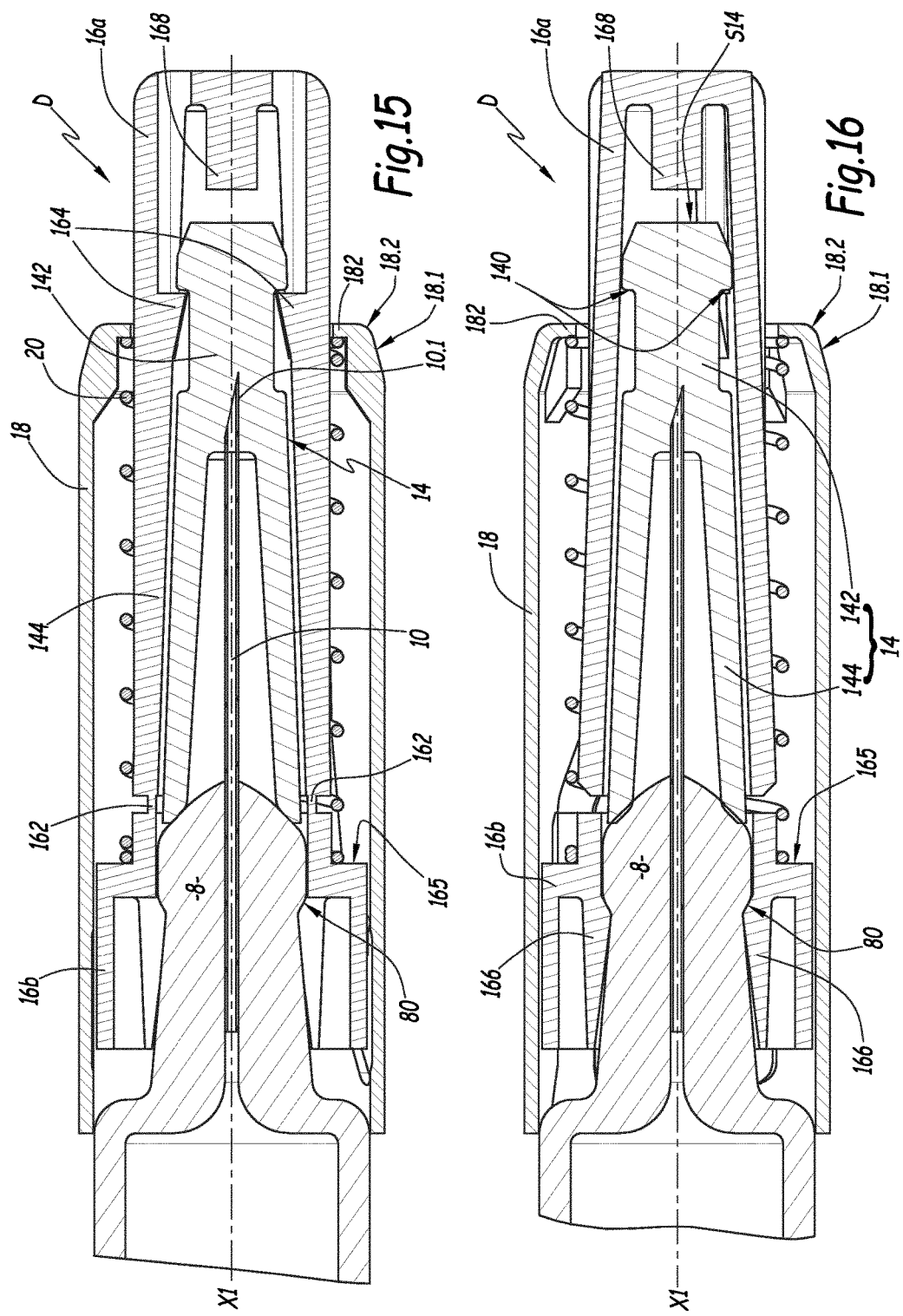

DEVICE FOR PROTECTING A NEEDLE, SYRINGE PROVIDED WITH SUCH A DEVICE, AND METHOD FOR PRODUCING PRE-FILLED CEMENTED NEEDLE SYRINGES

The invention relates to a device for protecting a needle, as well as a cemented needle syringe comprising such a device.

In a known manner, a device for protecting a needle, which may be better known under the name "post-use safety device", serves to protect the needle of a syringe at the end of an injection. This makes it possible to avoid injury with the needle when the latter is removed from the patient's body and to combat the transmission of diseases, such as HIV.

For example, GB-A-2,114,006 discloses an injection gun for animals. This gun is intended for repeated use on several animals. It comprises a sleeve that surrounds a needle and that includes two telescoping tubes. A spring keeps the inner tube in a position where it covers the needle. A cap makes it possible to protect the needle. This cap includes two parts that encapsulate an end-piece impregnated with sterilizing liquid and a detachable part, which is provided to be detached from the rest of the cap by applying a torque. Once the detachable part is removed, the cap defines a passage opening for the needle. During an injection, the gun is pressed against the animal's skin, which results in retracting the inner tube inside the outer tube. The needle then passes through the sterilized end-piece to penetrate the animal's skin. When the injection gun is removed from the animal, the inner tube returns to the position covering the needle, which is sterilized in contact with the end-piece. The risk of transmitting diseases from one animal to another is thus reduced. The injection gun of GB-A-2,114,006 is not intended for a single use. Thus, after an injection, the inner tube can again be retracted inside the outer tube to expose the needle. This is not compatible with a single-use syringe, with which the needle must remain protected after an injection.

Furthermore, WO-A-2013/134465, which constitutes the closest prior art, discloses a post-use safety device for a syringe. This device comprises a collar fastened around the nose of the syringe. A flexible needle shield is used as a cap and serves to keep the needle clean, i.e., to avoid contamination of the active ingredient contained in the syringe, and to protect the needle against any outside mechanical attack. The device comprises an outer sleeve that is movable along a longitudinal axis of the syringe against an elastic force generated by a spring, between a forward position, where it covers the needle, and a withdrawn position, where the needle is exposed. The collar comprises two outer pins, which are each engaged in a guide of the sleeve. When a shot is given, the flexible needle shield is removed and the sleeve is manually moved back to an intermediate position, prior to the injection, in which part of the needle protrudes from the end of the sleeve. When the syringe is brought against the epidermis, the needle penetrates the epidermis and the sleeve enters the withdrawn position. When the injection is complete and the needle is withdrawn from the patient's body, the sleeve is returned to the forward position so as to prevent the needle from being exposed at the end of the injection and someone from being stuck with said needle. One drawback of this device is that the outer sleeve and the needle shield must be assembled separately on the syringe, since the needle shield is not integrated into the safety device. More specifically, the needle shield is assembled by the glass worker, while the safety device is most often assembled by the pharmaceutical laboratory. Another drawback is that when the sleeve is an intermediate position, the needle is exposed and there is a risk of accidentally being stuck.

To that end, the invention relates to a device for protecting a needle, suitable for being mounted on a nose of a body of a cemented needle syringe, this device comprising:
- an outer sleeve, which is movable along a longitudinal axis between a forward position, where the outer sleeve covers the needle, and a withdrawn position, where the outer sleeve does not cover the needle,
- return means for returning the outer sleeve to the forward position, and
- means for locking the outer sleeve in the forward position at the end of an injection, wherein:
- the device further comprises a rigid needle shield including a flexible end-piece enclosed in a rigid sheath, this rigid sheath comprising a first part and a second part, which is detachable from the first part by a rotational movement relative to the first part, the first part of the rigid sheath comprising elastic fastening means around the nose of the syringe, which make it possible to secure the first part of the rigid sheath and the syringe body in rotation,
- the two parts of the sheath are connected to one another by sectile bridges, designed to be broken when a relative torque is applied between the two parts of the rigid sheath,
- the second part of the sheath protrudes from the outer sleeve, so as to be able to be rotated by a user and detached from the first part, the outer surface of the flexible end-piece and the inner surface of the rigid sheath being separated by play, such that the flexible end-piece does not risk rotating jointly with the second part of the sheath by friction, and
- the device further comprises translatable connecting means for translatable connection between the flexible end-piece and the second part of the rigid sheath, configured such that the flexible end-piece and the second part of the rigid sheath can be removed jointly from the cemented needle syringe without rotating the flexible end-piece around the needle.

Owing to the invention, the needle shield is directly integrated into the needle protection device, i.e., the safety device. This device therefore makes it possible to perform, aside from its primary function of protecting the needle at the end of injection, the functions related to the needle shield, i.e., preventing the contamination of the active ingredient before use and protecting the needle against any outside mechanical attack. Furthermore, the needle shield and the sleeve are assembled at the same time on the syringe body, which simplifies the method for manufacturing the syringe. Furthermore, because the needle is generally beveled, shavings of material can be formed if the end-piece in which the needle is pushed rotates around the needle. Yet the end-piece is not secured in rotation with the rigid sheath. Thus, a mechanical torque may be applied on the sheath to detach the parts of the sheath from one another, without the end-piece being rotated. The needle shield, or at least part of it, may therefore be separated from the device without shavings forming inside the needle.

According to advantageous, but optional aspects of the invention, the device may incorporate one or more of the following features, considered in any technically allowable combination:

The two parts of the sheath are connected to one another by sectile bridges, designed to be broken when relative torque is applied between the two parts of the sheath.

The fastening means include elastic tabs, designed to be elastically snapped around the nose of the syringe.

The translatable connecting means include teeth arranged on an inner radial surface of the sheath, which cooperate with a radial shoulder of the end-piece.

The sleeve is opaque and defines at least one recess forming a guide for a pin supported by a first part of the sheath.

The return means of the sleeve comprise a helical spring having a winding direction to the right.

An outer enclosure surface of the device has a diameter smaller than 9.3 mm, preferably equal to 9 mm.

The invention also relates to a cemented needle syringe, comprising a needle protection device as previously described.

Currently, pre-filled cemented needle syringes are manufactured as follows: The glass worker manufacturing the glass syringe bodies attaches a flexible or rigid needle shield to the end of each cemented needle syringe body. The syringe bodies, then each equipped with a needle shield, are next placed in a plastic support, called "rack". This rack is in fact a plate defining a series of receiving holes for the syringe bodies. The racks are next positioned in transfer containers, which are sealed using a synthetic film. The containers are sterilized using ethylene oxide, which can traverse the sealing membrane. When the containers are received by the pharmaceutical laboratory, they are opened in a sterile atmosphere and the racks are taken out and placed on automatic filling machines. Each syringe body is filled with an active ingredient, then a plunger, also called "plunger seal", is pushed inside each syringe body. The syringe bodies are then removed from the racks to place them on an inspection and labeling line. Once this operation is done, the syringe bodies are moved onto another assembly line to incorporate safety system and a pushing rod of the plunger therein, which is able to activate the safety system once the injection is complete.

The major drawback of this method is that it is necessary to invest in cumbersome and costly infrastructure to equip the syringes with a post-use safety system. Another drawback is that the selected safety system is particularly cumbersome, such that the syringes cannot be packaged with a standard primary packaging (blister) or a standard secondary packaging (cardboard box). In particular, the final packaging is particularly cumbersome, which causes a high transportation cost. Lastly, the pushing rod of the plunger used is not standard, since it includes washers to activate the safety system once the injection is complete.

WO-A-2011/110872 discloses a method for manufacturing pre-filled cemented needle syringes, wherein the syringe bodies are positioned inside housings provided in a holder. Each syringe body is equipped with a needle shield and a post-use safety system. The holder of the syringe bodies is placed in a container, which is closed and sterilized. The holder of the container is next removed in a sterile environment so as to fill each syringe body with an active ingredient. The holder used is a specific holder, in which the housings are configured to ensure centering of the syringe bodies. The drawback of this method is therefore that the holder is not a standard holder, with holes having a diameter of 9.3 mm.

The invention more particularly aims to resolve these drawbacks by proposing a method for manufacturing pre-filled syringes that can be implemented with a less cumbersome and less costly installation.

To that end, the invention also relates to a method for manufacturing pre-filled cemented needle syringes, comprising the following steps:

a) mounting a needle protection device as described above on syringe bodies, b) positioning the syringe bodies, equipped with the protection device, in housings provided in a holder, c) placing the holder in a standard container, closing the container and sterilizing the container for transport, d) in a sterile atmosphere, removing the holder from the container, e) filling each syringe body with an active ingredient, wherein the protection devices are compact enough to traverse the housings of a standard holder, which have a diameter of 9.3 mm, and wherein the method further comprises the following steps:

f) inserting a plunger into each syringe, g) removing the syringes from their holder for inspection, assembling a plunger rod and the label, and h) individually packaging each syringe with a primary packaging and a secondary packaging.

Owing to this method, the device for protecting the needle can be placed directly by the glass worker, i.e., at the same time as the needle shield, since the latter is integrated into the device. The pharmaceutical laboratories therefore do not need to provide a dedicated assembly lines for mounting the post-filling safety system. This makes it possible to save space in the syringe assembly infrastructure. Furthermore, the protection device integrating the needle shield is compact enough for the syringes to be able to be positioned, in step b), with their protection device in a standard holder, or rack. Likewise, standard plunger rods can be used. The final packaging is also standard and compact. Thus, the existing industrial manufacturing method is not disrupted, but on the contrary, made easier.

Advantageous, but optional features of the invention are defined below:

Step a) is carried out by a glass worker manufacturing syringe bodies.

In step c), the holder is placed in the container such that the syringes do not touch the bottom of the container.

The device mounted on each syringe body has, at its distal end, an annular bevel that cooperates, without snags, with a corresponding housing of the holder during steps b) and g).

In step g), the plunger rod is screwed on the plunger.

The primary packaging used in step g) is a transparent shell packaging.

The secondary packaging used in step g) is a cardboard box.

Each device comprises elastic fastening means on a corresponding syringe body, which are fastened, during step a), by approaching the syringe body.

The fastening means include elastic tabs that cooperate, during step a), with an end part of the syringe body, this end part being configured to block the release of the tabs once the device is mounted.

Steps d) to f) are automated.

Figure 20:
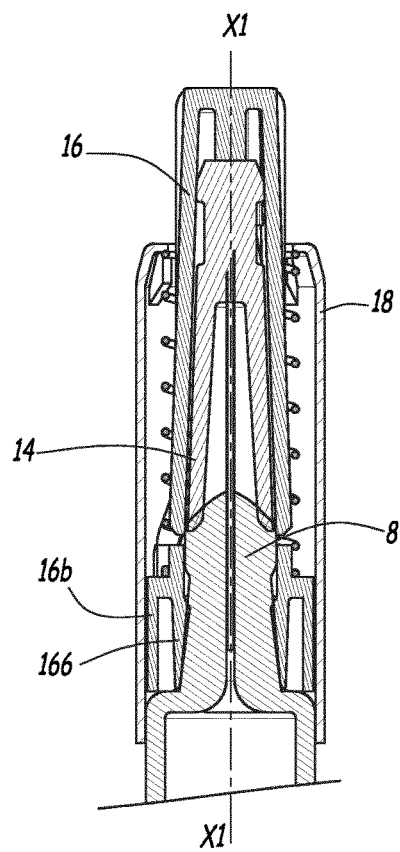
Figure 21:
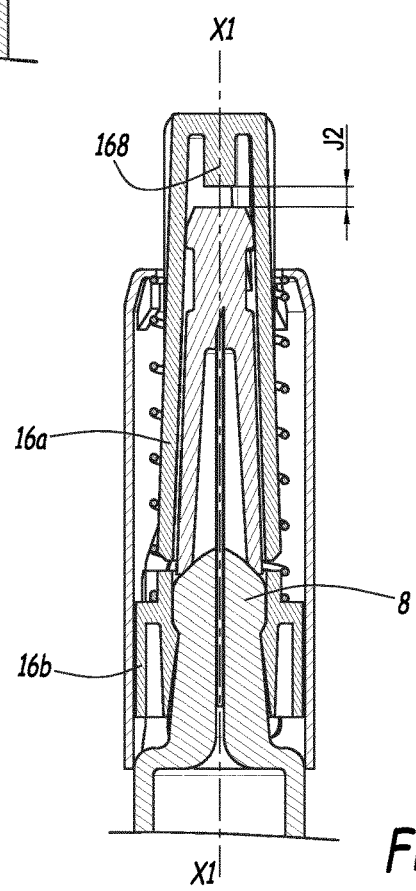
Figure 22:
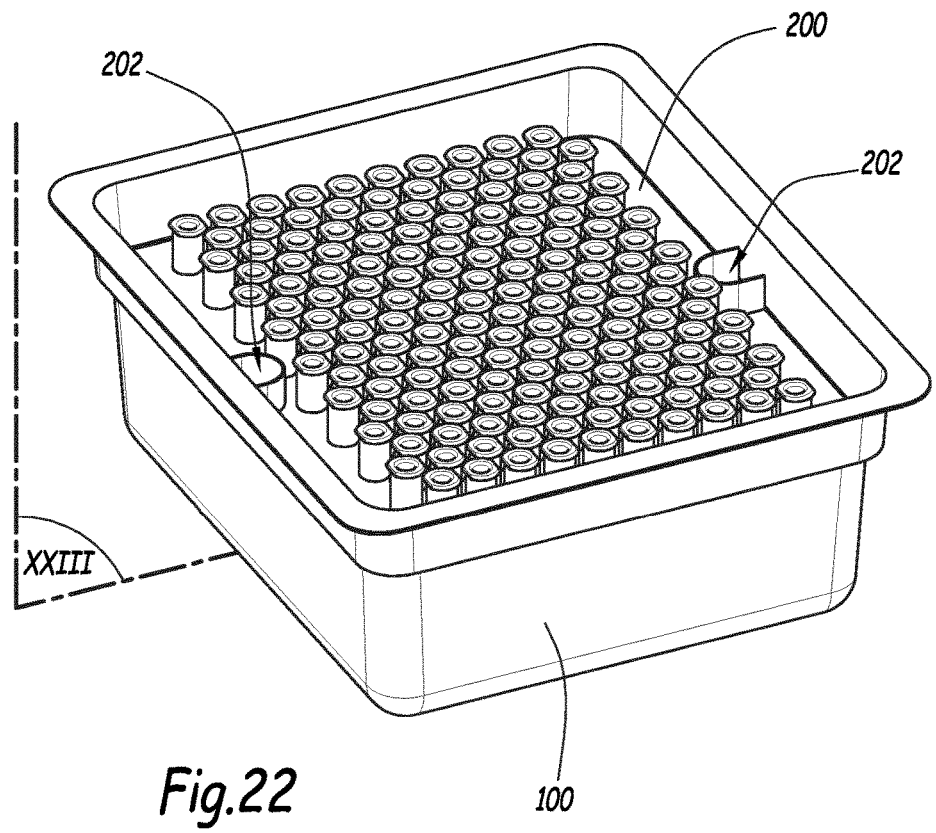
Figure 23:
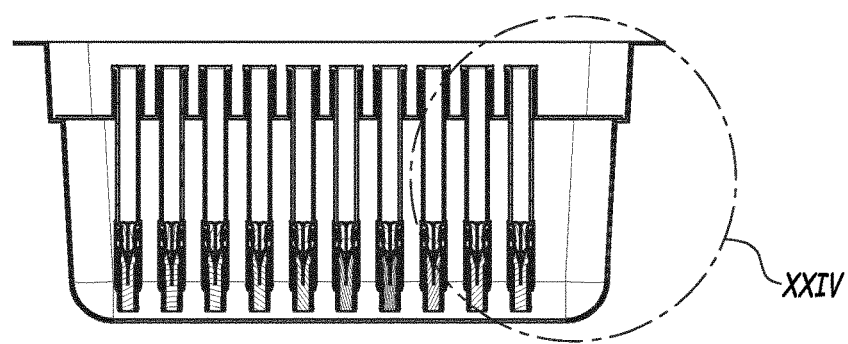
Figure 24:
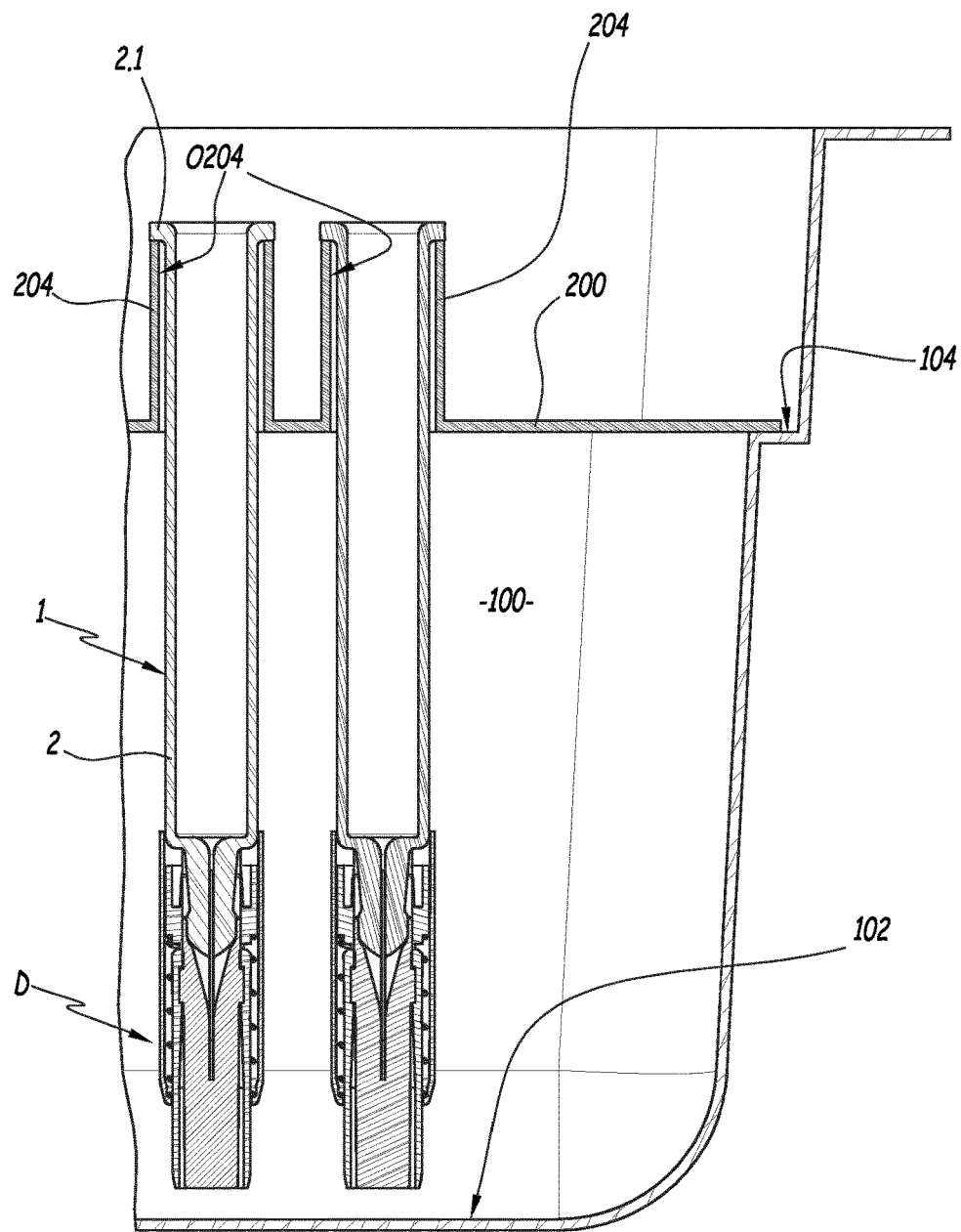

The invention and other advantages thereof will appear more clearly in light of the following description of one embodiment of a device for protecting a needle and a manufacturing method according to their principle, provided solely as an example and done in reference to the appended drawings, in which:

FIGS. 1, 3, 5, 7, 9, 11 and 13 each show a side view of a cemented needle syringe, comprising a device for protecting a needle according to the invention, FIGS. 2, 4, 6, 8, 10, 12 and 14 each show a longitudinal sectional view, on a larger scale, of the syringe corresponding to the figures set out above, FIGS. 15 and 16 are enlarged longitudinal sectional views of the protection device of the syringe of FIGS. 1 to 14, in two different cutting planes, FIGS. 17 to 21 are longitudinal sectional views showing assembly steps of the device of FIGS. 1 to 16 on a cemented needle syringe, FIG. 22 is a perspective view showing a transport container for manufacturing cemented needle syringes as shown in FIG. 1, FIG. 23 is a sectional view along plane XXIII of FIG. 22, FIG. 24 is an enlarged view of circle XXIV of FIG. 23, and FIGS. 25 to 27 are perspective views each showing a step of the manufacturing method according to the invention.

Each of FIGS. 1 to 14 shows a cemented needle syringe 1. This syringe 1 is of the pre-filled type and extends along a longitudinal axis X1. It comprises a syringe body 2, generally made from glass, that is globally tubular and centered on the axis X1. The body 2 includes a nose 8 in which a hollow needle 10 is pushed. The needle 10 is fastened to the inside of the nose 8 by gluing. The nose 8 has an outer recess 80. The needle 10 includes a beveled distal end 10.1. The syringe body 2 contains an active ingredient P, such as a medicinal product. The syringe 1 also includes a standard rod 4 that is equipped at its end with a seal 6. The seal 6 serves as a plunger to inject the active ingredient P through the hollow needle 10, which is why the seal 6 is commonly called "plunger" or "plunger seal". The seal 6 is attached to the rod, i.e., it is connected in translation with the rod 4 in both movement directions. More specifically, the rod 4 is screwed to the inside of the seal 6. Opposite the seal 6 along the axis X1, the rod 4 is equipped with a vane 42 on which the user can exert a pushing force toward the nose 8. The rod 4 is translatable relative to the body 2 along the axis X1, i.e., it is able to slide inside the syringe body 2.

In this description, the front or distal direction refers to a direction parallel to the longitudinal axis X1 and turned toward the epidermis of the patient under normal usage conditions of the syringe 1, while the rear or proximal direction is oriented in the opposite way relative to the injection zone, on the side of the vane 42.

The syringe 1 includes, in the front, a device D for protecting the needle 10. This device D is suitable for being mounted on the front end of the syringe body. The device D incorporates a needle shield 12 that makes it possible on the one hand to keep the needle 10 clean before the use of the syringe 1 and to thus prevent the pollution of the active ingredient P, and on the other hand to protect the needle 10 against any outside mechanical action. For example, the needle shield 12 prevents the needle 10 from twisting or breaking before use.

The needle shield 12 is a rigid needle shield comprising a flexible end-piece 14 in which the needle 10 is pushed and a rigid sheath 16 that surrounds the end-piece 14. The end-piece 14 is made from elastomer (rubber) or injectable thermoplastic material, while the rigid sheath 16 is made from plastic, in the example, high-density polyethylene (HDPE). The needle shield 12 is more visible in FIGS. 15 and 16. As shown in these figures, the end-piece 14 includes, in the front, a narrower section 142 forming an annular shoulder 140 that widens the diameter of the end-piece 14 going toward the front. The end-piece 14 also includes, in the rear, a skirt 144 surrounding part of the needle 10. The end-piece 14 is compressed against the nose 8 of the syringe body 2. The skirt 144 is frustoconical and becomes wider toward the rear of the end-piece 14.

The rigid sheath 16 is made from two parts 16a and 16b that are detachable from one another by a relative rotational movement between the two parts 16a and 16b. Indeed, the two parts of the sheath 16a and 16b are connected to one another by sectile bridges 162, designed to be broken when relative torque M1 is applied between the two parts of the sheath 16a and 16b. The part 16a is positioned in front of the part 16b. The parts 16a and 16b are each tubular and centered on the longitudinal axis X1.

The rear part 16b of the sheath 16 is snapped around the nose 8 of the syringe 1, i.e., it comprises an elastic fastening means around the nose 8 of the syringe 1. These fastening means comprise elastic tabs 166 that are configured to be jammed in the recess 80 of the nose 8. The part 16b is therefore secured in rotation with the syringe body 2. The rear part 16b of the rigid sheath 16 also includes two diametrically opposite ends 160, which protrude radially outward relative to the longitudinal axis X1. Only one of these pins, however, is visible in the figures.

The device D comprises translatable connecting means, along the axis X1, between the end-piece 14 and the part 16a of the sheath 16. These connecting means include teeth 164 arranged on an inner radial surface of the front part 16a of the sheath. These teeth 164 protrude radially relative to the longitudinal axis X1 toward the inside of the sheath and cooperate with the annular rim 140 of the end-piece 14, such that the end-piece 10 is connected in translation with the front part 16a of the sheath 16. However, a rotation of the sheath 16 around its axis does not cause the end-piece 14 to rotate, i.e., the sheath 16 and the end-piece 14 are not secured in rotation around the longitudinal axis X1. The front part 16a of the sheath 16 includes, at its front end, a central lug 168 extending axially toward the rear. Axial play J2 of about 1 mm exists between the lug 168 and a front end surface S14 of the end-piece 14. The play J2 is measured parallel to the axis X1. Furthermore, there is play between the outer surface of the end-piece 14 and the inner surface of the sheath 16. This play is measured along a direction normal to the outer surface of the end-piece 14, which is slightly oblique relative to the axis X1. Thus, the end-piece 14 does not risk rotating jointly with the front part 16a of the sheath 16 by friction.

The protection device D also includes a safety system seeking to protect the needle 10 after use of the syringe 1, i.e., when the syringe 1 removed from the patient's body. This system comprises an outer sleeve 18, which is positioned coaxially around the rigid sheath 16. The sleeve 18 is made from an opaque material, to completely hide the needle 10. This sleeve 18 defines an inner radial rim 182 at its front end and two recesses 180 in which the pins 160 are respectively inserted. In the example, the pins do not protrude from the recesses 160 toward the outside. The recesses 180 serve as a guide for the pins 160. Each recess 180 is globally in the shape of an asymmetrical Y, with the branches of the Y extending toward the rear. The branches of the Y are referenced 180a and 180c, while its central portion is referenced 180b. This central portion 180b is a straight portion, i.e., a corridor. The device D also comprises means for locking the sleeve 18 in the forward position, which are activated at the end of an injection. In the example, these locking means are formed by a housing 180d that extends, from the branch 180c, in the forward direction.

The outer sleeve 18 is axially movable, i.e., along the axis X1, between a forward position, where it covers the needle 10, and a withdrawn position, where the needle 10 is exposed. The safety system comprises elastic return means for returning the outer sleeve 18 to the forward position. These return means comprise a helical spring 20 that is inserted between the inner radial rim 182 of the sleeve 18 and a shoulder 165 formed on the rear part 16b of the rigid sheath 16. The helical spring 20 has a RH thread, i.e., the winding direction of the spring 20 is to the right. This means that the spring 20 is wound to the right, or in the clockwise direction, when one looks at the spring 20 from the bottom of FIGS. 1 to 14, i.e., from the rear side.

Radial mechanical play exists between the outer sleeve 18 and the rigid sheath 16, such that the sleeve 18 can slide around the sheath 16 without friction. Conversely, there is little or no radial mechanical play between the sleeve 18 and the outer surface of the syringe body 2, such that the device D is radially not very cumbersome. In particular, the thickness of the sleeve 18 is chosen so that the syringes 1 can be inserted into the holes of a standard holder.

Furthermore, the sleeve 18 includes, at its distal end, an annular bevel 18.1 that converges relative to the central axis of the sleeve 18 in the forward direction and that is connected to the inner radial rim 182 by a peripheral hollow 18.2. Below, different usage steps of the syringe 1 are described in reference to FIGS. 1 to 14.

Figure 2:
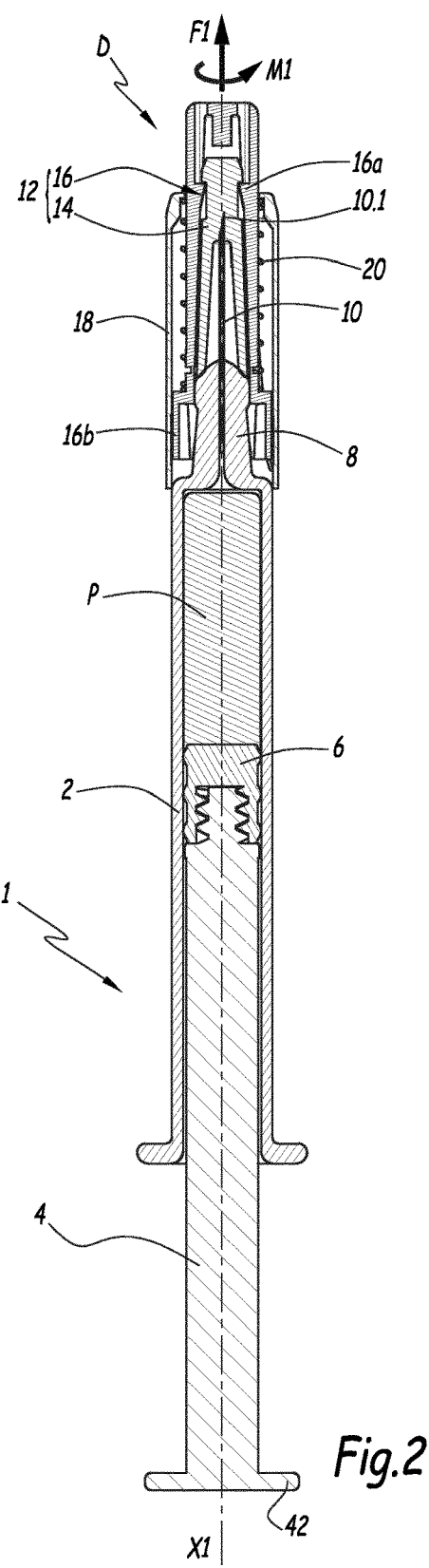

First of all, the user must remove the rigid needle shield 12 to be able to perform the injection. To that end, he applies the torque M1 around the axis X1, as shown in FIG. 2, to rotate the front part 16a relative to the rear part 16b and break the bridges 162. Once the bridges 162 are broken, the user can remove the front part 16a of the rigid sheath 16, as shown by arrow F1 in FIG. 2. The removal of the part 16a jointly drives the removal of the end-piece 14 by cooperation of the teeth 164 with the annular rim 140 of the end-piece 14. Thus, the end-piece 14 and the front part 16a of the sheath 16 are removed from the syringe 1 without rotating the end-piece 14 around the needle 10, such that the distal end 10.1 of the needle 10, which is beveled, does not form shavings of material that may penetrate the needle 10.

The removal of the end-piece 14 and the front part 16a of the sheath 16 brings the syringe 1 into the configuration of FIGS. 3 and 4. In this configuration, the needle 10 is completely covered by the sleeve 18. As long as the syringe 1 has not been used, the pins 160 of the rear part 16b of the sheath 16 are housed in the branch 180a of the recesses 180.

Figure 5:
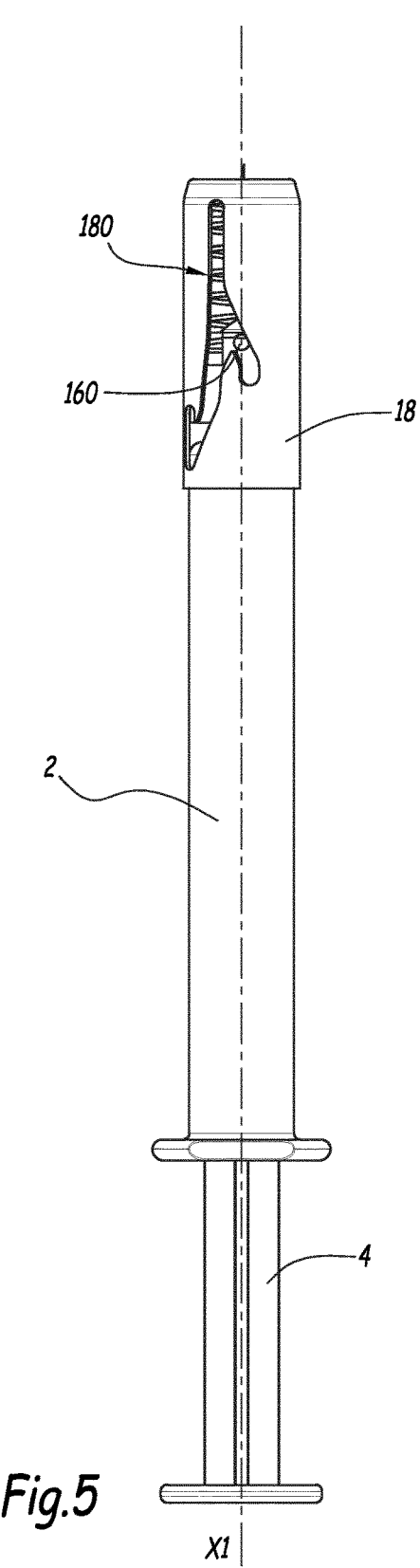
Figure 6:
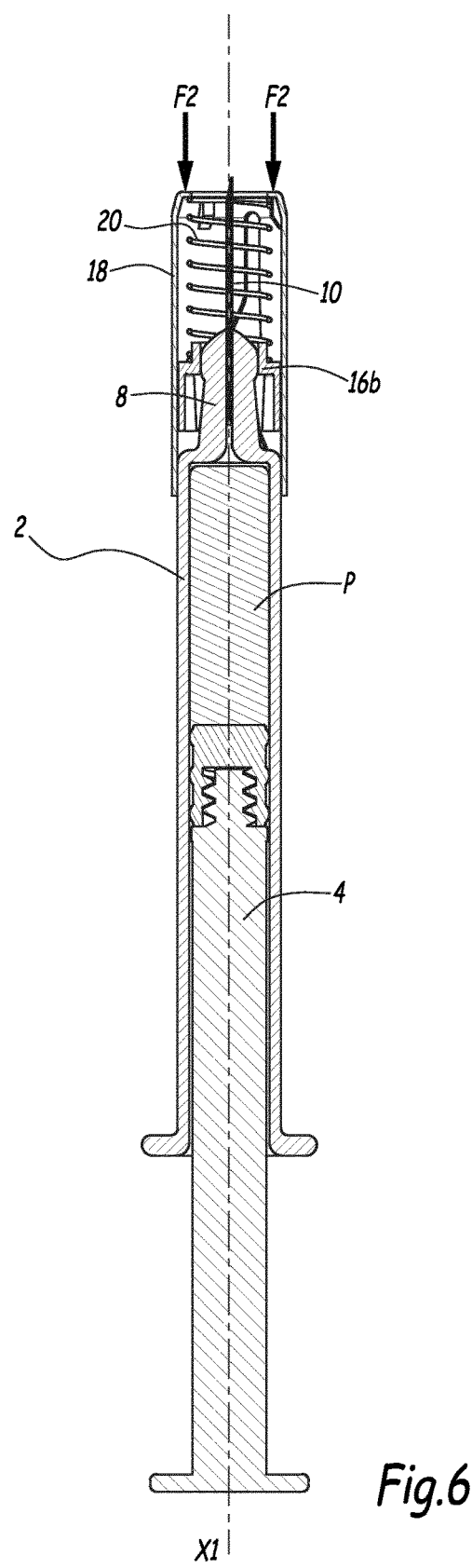

In reference to FIGS. 5 and 6, when the syringe 1 is brought against the epidermis of the patient, the pressure exerted by the sleeve 18 on the skin drives the withdrawal of the sleeve 18, as shown by the arrows F2 in FIG. 6. The spring 20 is then compressed, the needle 10 penetrates the epidermis and the pins 160 move from the branch 180a into the central portion 180b. The sleeve 18 withdraws around the syringe body 2. Thus, the needle 10 is not exposed as long as the syringe 1 is not brought against the patient's epidermis, unlike the materials according to WO-A-2013/134465 and WO-A-2007/077463, where the needle is partially exposed before the syringe is brought against the patient's body. In other words, the sleeve 18 is not withdrawn prior to the injection to expose the needle 10. Thus, there is no risk of accidental sticking before the injection. Continuing the movement brings the outer sleeve 18 toward its withdrawn position, in which it no longer covers the needle 10. The movement is continued until the pins 160 reach the bottom of the corridor 180b of the recesses 180, as shown in FIGS. 7 and 8.

Figure 7:
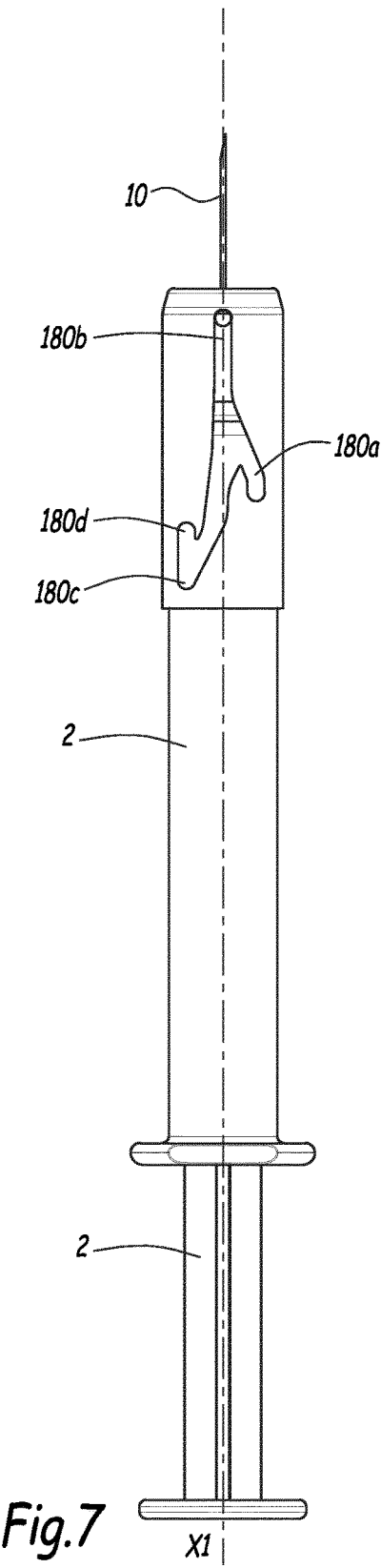
Figure 8:
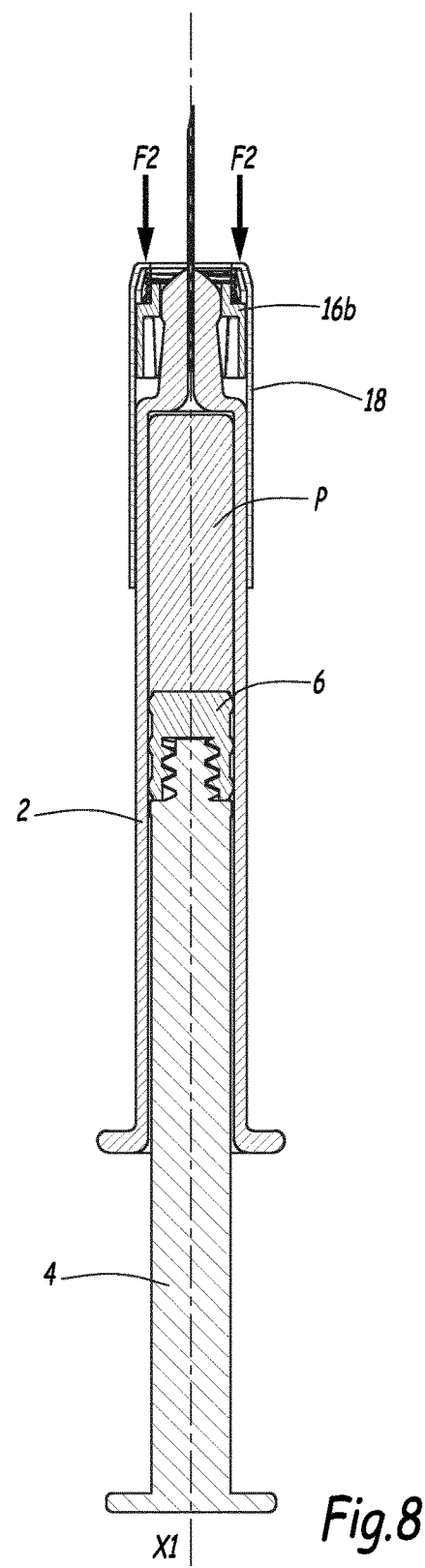

In the configuration of FIGS. 7 and 8, the needle 10 of the syringe 1 is completely pushed into the patient's epidermis. The user can then press on the vane 42 of the rod 4 to eject the active ingredient P contained inside the syringe 1 into the patient's body, as shown by arrow F4 in FIG. 10.

When the user removes the syringe 1 from the patient's body, the outer sleeve 18 is elastically returned to the forward position by the spring 20, as shown by the arrows F3 in FIG. 10. The outer sleeve 18 then returns to cover the needle 10 and the pins 160 slide in the corridor 180b of the recesses 180 toward the branch 180c. The syringe 1 is then in the configuration of FIGS. 11 and 12, which corresponds to an end of injection configuration.

If, after use of the syringe 1, a clumsy user presses on the sleeve 18, i.e., tries to withdraw the sleeve 18, the pins 160 then move into the housing 180d of the recesses 180 and the movement of the sleeve 18 toward the rear is blocked, as shown in FIGS. 13 and 14. This constitutes an additional safety, since the needle 10 can no longer be exposed at the end of the injection. More specifically, the movement of the pins 160 of the branch 180c toward the housing 180d is favored because the spring 20 has a right winding direction. Indeed, when this spring 20 is compressed, it exerts a torque on the sleeve 18 that is oriented, due to its winding direction, in a counterclockwise direction when seen from the top in FIG. 11, i.e., when looking at the syringe 1 from the needle 10 side. This torque makes it possible to prevent the pins 160 from returning toward the corridor 160b if the user tries to remove the sleeve 18 after the injection. This torque also makes it possible to guide the pins 160 correctly in the corridor 180b up to the branch 180c of the recesses 180.

Figures 17, 18:
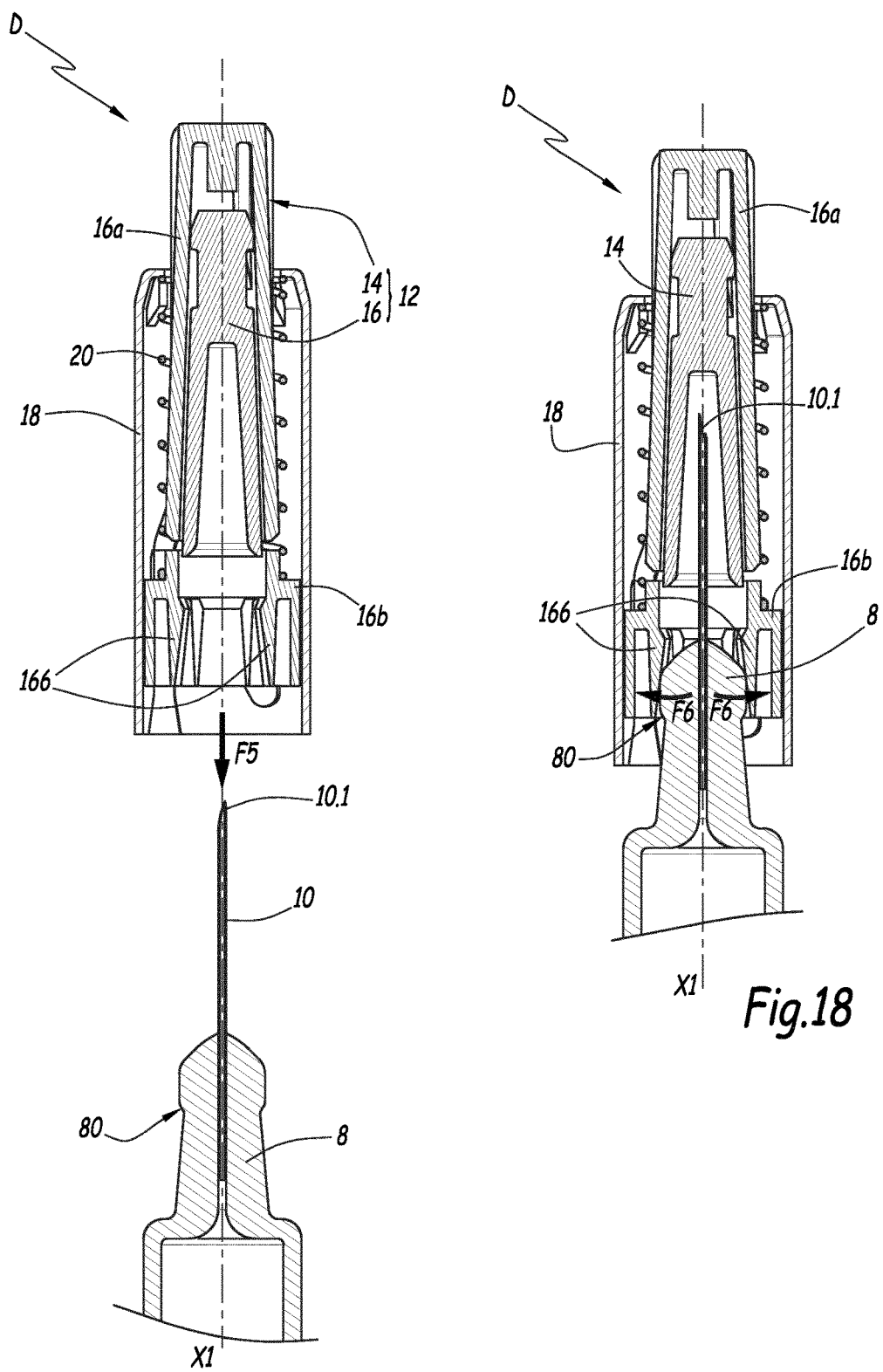

FIGS. 17 to 21 show the steps for mounting the protection device D on the nose 8 of the syringe body 2. A first step for mounting the protection device D consists of bringing the device D closer to the nose 8, as shown by arrow F5 in FIG. 17. By continuing the approach movement in the direction of the arrow F5, the elastic tabs 166 are then deformed along a centrifugal radial direction F6 in contact with the nose 8, as shown in FIG. 18. Once the tabs 166 have gone past the recess 80 of the nose 8, they snap against the latter by elastic return of the material, as shown by the arrows F7 in FIG. 19. The nose 8 of the syringe 1 is configured to block the release of the tabs 166. A play J1 of about 1.5 mm exists between the free end of the tabs 166 and the syringe body 2. The play J1 is measured parallel to the axis X1.

Figure 19:
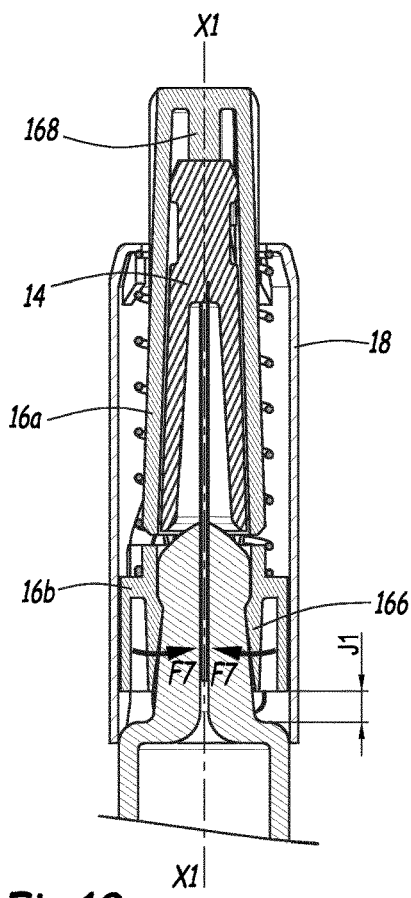

During a final step illustrated by FIGS. 19 to 21, one presses on the needle shield 12 so as to push the needle 10 firmly inside the end-piece 14. As shown in FIG. 20, the end-piece 14 is then axially compressed, between the lug 168 of the rigid sheath 16 and the nose 8 of the syringe body 2, and the play J1 between the free end of the tabs 166 and the syringe body 2 is reacted. When the pressure is released on the needle shield 12, the material of the end-piece 14 regains its initial shape and pushes the sheath 16 back in the forward direction. The sheath 16 then returns to the snapping position, and axial play J2 exists between the front end surface S14 of the end-piece 14 and the lug 168.

Below, a method is described, in reference to FIGS. 22 to 27, for manufacturing pre-filled cemented needle syringes 1, as previously described. In the present document, a part is considered "standard" if it is already commercially available, i.e., if it is already used in the existing manufacturing methods.

The method comprises a first step a) consisting of mounting a protection device D on each cemented needle syringe 1. This first step a) is carried out by a glass worker manufacturing syringe bodies 2. Since the protection device D incorporates the needle shield 12, the safety system and the needle shield 12 are mounted in a single piece on the syringe body 2. This makes it possible to simplify the existing assembly method. Furthermore, owing to the elastic fastening means, the mounting of the device D on the syringe body 2 is done simply by bringing the two elements closer together. A second step b) consists of positioning the syringes 1, each equipped with a protection device D, in housings O204 provided in a standard holder 200. This holder 200 is commonly called "rack" and consists of a plastic rectangular plate with holes. The holes O204 of the plate 200 form receiving housings for the syringes 1. The holes O204 have a diameter smaller than the diameter of an outer enclosure surface of the device D. In a standard manner, these holes O204 have a diameter of 9.3 mm. An outer enclosure surface of the device D has an outer diameter that is therefore smaller than 9.3 mm, in the example about 9 mm. The holes 204 are defined by pillars 204 that protrude upward perpendicular to the plate 200. The holder 200 defines sixteen rows of ten holes O204.

Owing to the presence of the bevel 18.1 and the hollow 18.2 that are provided at its distal end, each device D is inserted with no snags in a housing O204 of the holder 200. In other words, when the syringes are inserted into the holder 200, the outer surface of the sleeve 18 slides against the wall of the corresponding hole O204.

The body 2 of each syringe includes, at an end opposite the nose 8, an annular shoulder 2.1 provided to bear against the free end of a pillar 204, so as to prevent the syringe body 2 from falling under the effect of gravity. The plate 200 includes two handles 202 making it easier to grasp. When all of the syringes are positioned in the rack 200, the latter is positioned, during a third step c), inside a standard container 100. The container 100 to that end comprises two opposite shoulders 104, which each extend over an entire side of the container 100. As shown in FIGS. 23 and 24, the syringes 1 do not touch the bottom 102 of the container 100 when the rack 200 is placed in the container 100.

The container 100 is next sealed tightly using a synthetic film, not shown, which is not gas-tight. The container 100 is made sterile by gas injection, in particular ethylene oxide. The ethylene oxide penetrates the membrane of the container, which makes it possible to sterilize the syringes inside the container. At the end of step c), the containers 100 are sent by the glass worker to the pharmaceutical laboratory. In other words, the method comprises a step after step c) consisting of transporting the containers 100 from one point to another, in the case at hand from the glass worker to the pharmaceutical laboratory.

Figure 25:
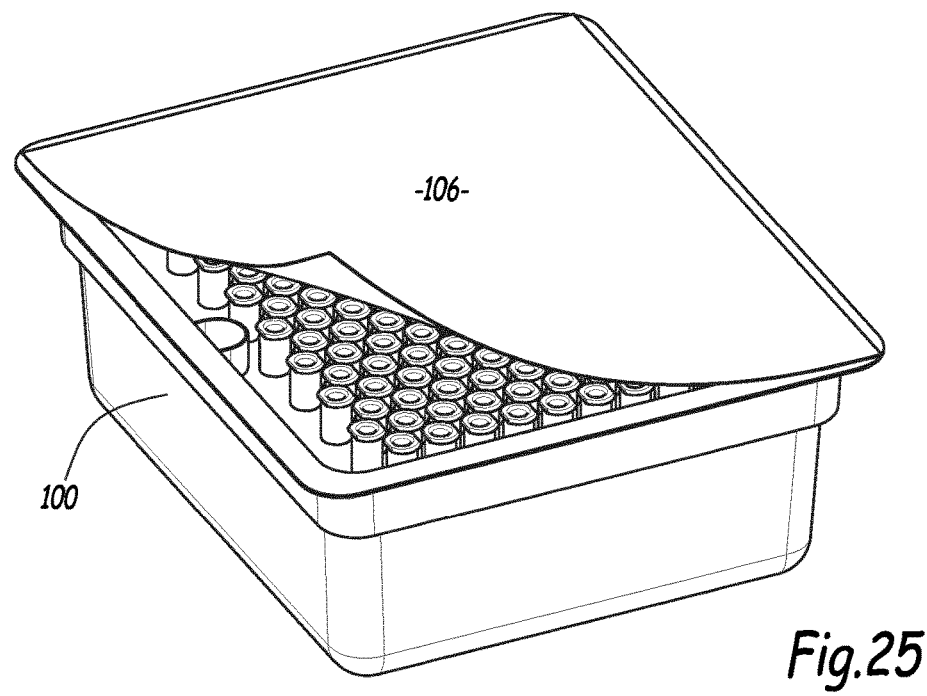
Figure 26:
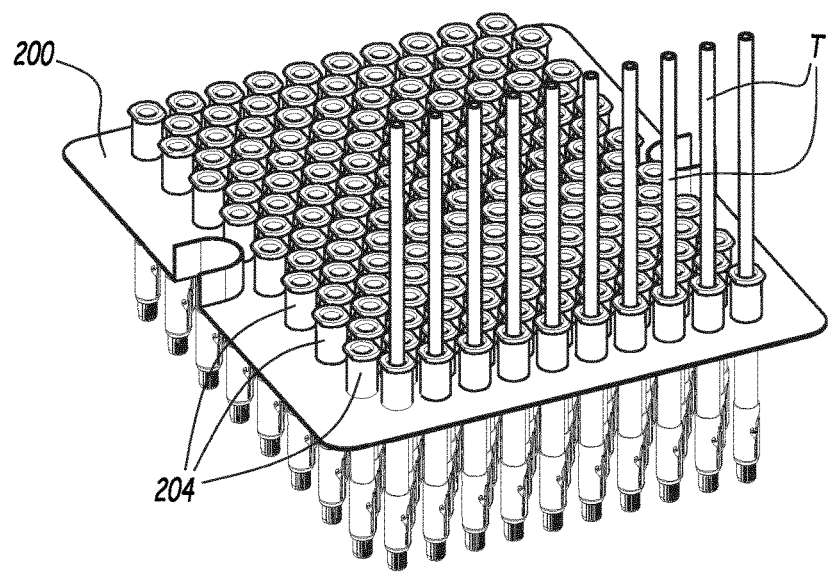

As shown in FIG. 25, the containers 100 are opened, during a fourth step d), at the pharmaceutical laboratory in a sterile environment and the racks 200 are automatically removed from the containers 100. During a fifth step e), the racks 200 are placed on automatic filling machines, not shown, to fill the syringe bodies 2 with an active ingredient P, such as a medicinal product. As shown in FIG. 26, the filling machine comprises a row of ten filling tubes T, suitable each for being inserted in a syringe body 2. The active ingredient is then injected through the tubes T. Once all of the syringe bodies of a row are filled, the tubes T are removed from the bodies 2 and the holder 200 is moved to fill another row of syringes.

Figure 27:
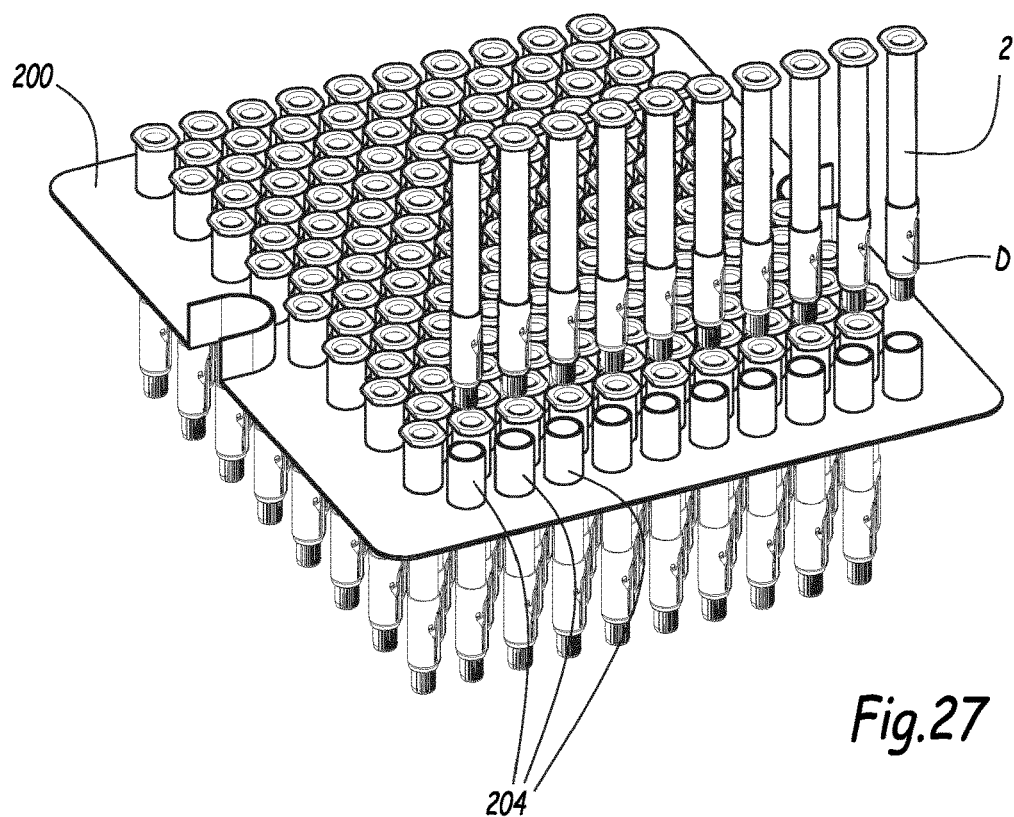

Once all of the syringes 1 are filled, a plunger, or plunger seal 6, is inserted during a sixth step f) inside each syringe body 2. As shown in FIG. 27, the bodies 2 of the syringes 1, then filled with active ingredient, are removed, during a second step g), from the racks 200. The removal of the syringes from the holder 200 is done without snags due to the presence of the annular bevel 18.1 and the hollow 18.2 on each device D. In other words, when the syringes are removed from the holder 200, the outer surface of the sleeve 18 slides against the wall of the corresponding hole O204. The syringes 1 next placed on a line for inspection, the assembly of the plunger rod 4 and the label. More specifically, the rod 4 is screwed in the seal 6.

During an eighth step h), the pre-filled syringes 1 are packaged individually with a primary packaging 300 and a secondary packaging 400. The primary packaging 300 is a standard transparent shell packaging, better known as a "blister". The secondary packaging 400 is a standard cardboard box. The packaged product is compact, and therefore easy to transport. These packages are shown, in dotted lines and solid lines, respectively, in FIG. 1 only.

Owing to this new method, the syringes 1 are delivered to the pharmaceutical laboratory with their protection device D integrated, such that the pharmaceutical laboratory is not required to assemble the protection device on each syringe. The pharmaceutical laboratory therefore does not need to have an assembly line dedicated to mounting the protection devices on the syringes, which makes it possible to save space. Furthermore, the protection device D is very compact, such that the syringe 1 can be positioned in a hole of the rack directly with the protection device.

In an alternative that is not shown, return means different from a spring can be considered to return the outer sleeve 18 into the forward end-of-injection position.

In an alternative that is not shown, a single recess 180 is formed in the sleeve 18. Likewise, the sleeve 18 can define a number of recesses 180 strictly greater than two, for example equal to three.

In an alternative that is not shown, the parts 16a and 16b of the sheath 16 can be screwed to one another or connected by a rotating locking mechanism. For example, the mechanism can comprise a pin guided in a curved or bent slot. This type of mechanism is commonly called bayonet locking mechanism. In all cases, the parts 16a and 16b that are detachable from one another by a relative rotational movement between the two parts.

In an alternative that is not shown, the plunger seal 6 is not attached to the rod 4, i.e., the rod 4 is in simple bearing against the seal 6. The seal 6 is then only connected to the rod 4 in one movement direction.

According to another alternative that is not shown, the container 100 defines an opening or a transparent part for viewing the syringes 1 from the outside.

The features of the alternatives and embodiments considered above may be combined with one another to create new embodiments of the invention.

The invention claimed is:

1. A device for protecting a needle, suitable for being mounted on a nose of a body of a cemented needle syringe, this device comprising:

an outer sleeve, which is movable along a longitudinal axis between a forward position, where the outer sleeve covers the needle, and a withdrawn position, where the outer sleeve does not cover the needle, return means for returning the outer sleeve to the forward position, and means for locking the outer sleeve in the forward position at an end of an injection, wherein:

the device further comprises a rigid needle shield including a flexible end-piece enclosed in a rigid sheath, this rigid sheath comprising a first part and a second part, which is detachable from the first part of the rigid sheath by a rotational movement relative to the first part of the rigid sheath, the first part of the rigid sheath comprising elastic fastening means around the nose of the cemented needle syringe, which make it possible to secure the first part of the rigid sheath and the body in rotation, the first and second parts of the rigid sheath are connected to one another by sectile bridges, designed to be broken when a relative torque is applied between the first and second parts of the rigid sheath, the second part of the rigid sheath protrudes from the outer sleeve, so as to be able to be rotated by a user and detached from the first part of the rigid sheath, the outer surface of the flexible end-piece and the inner surface of the rigid sheath being separated by play, such that the flexible end-piece does not risk rotating jointly with the second part of the rigid sheath by friction, and the device further comprises translatable connecting means for translatable connection between the flexible end-piece and the second part of the rigid sheath, configured such that the flexible end-piece and the second part of the rigid sheath can be removed jointly from the cemented needle syringe without rotating the flexible end-piece around the needle.

2. The device according to claim 1, wherein the fastening means include elastic tabs, designed to be elastically snapped around the nose of the cemented needle syringe.

3. The device according to claim 1, wherein the translatable connecting means include teeth arranged on an inner radial surface of the rigid sheath, which cooperate with a radial shoulder of the flexible end-piece.

4. The device according to claim 1, wherein the outer sleeve is opaque and defines at least one recess forming a guide for a pin supported by the first part of the rigid sheath.

5. The device according to claim 1, wherein the return means of the outer sleeve comprise a helical spring having a right winding direction.

6. A cemented needle syringe, wherein the cemented needle syringe comprises a device for protecting the needle according to claim 1.

7. A method for manufacturing pre-filled cemented needle syringes, comprising the following steps:
 a) mounting a needle protection device according to claim 1 on syringe bodies,
 b) positioning the syringe bodies, equipped with the needle protection device, in housings provided in a holder,
 c) placing the holder in a standard container, closing the standard container and sterilizing the standard container for transport,
 d) in a sterile atmosphere, removing the holder from the standard container,
 e) filling each syringe body with an active ingredient, wherein the protection devices are compact enough to traverse the housings of a standard holder, which have a diameter of 9.3 mm, and wherein the method further comprises the following steps:
 f) inserting a plunger into each syringe,
 g) removing the pre-filled cemented needle syringes from their holder for inspection, assembling a plunger rod and a label of the syringes, and
 h) individually packaging each pre-filled cemented needle syringe with a primary packaging and a secondary packaging.

8. The method according to claim 7, wherein, in step c), the holder is placed in the standard container such that the syringes do not touch a bottom of the standard container.

9. The method according to claim 7, wherein the needle protection device mounted on each syringe body has, at its distal end, an annular bevel that cooperates, without snags, with a corresponding housing of the holder during steps b) and g).

10. The method according to claim 7, wherein, in step g), the plunger rod is screwed on the plunger.

11. The method according to claim 7, wherein the primary packaging used in step g) is a transparent shell packaging.

12. The method according to claim 7, wherein the secondary packaging used in step g) is a cardboard box.

13. The method according to claim 7, wherein each needle protection device comprises elastic fastening means on a corresponding syringe body, which are fastened, during step a), by approaching the syringe body.

14. The method according to claim 7, wherein steps d) to f) are automated.

15. The method according to claim 13, wherein the fastening means include elastic tabs that cooperate, during step a), with an end part of the syringe body, this end part being configured to block the release of the elastic tabs once the needle protection device is mounted.

* * * * *